United States Patent [19]

Viscomi et al.

[11] Patent Number: 5,244,655
[45] Date of Patent: Sep. 14, 1993

[54] PROCESS FOR THE PURIFICATION OF RECOMBINANT HUMAN BETA INTERFERON, BETA INTERFERON THUS PURIFIED AND PHARMACEUTICAL COMPOSITIONS WHICH CONTAIN IT

[75] Inventors: Giuseppe C. Viscomi, Siena; Paolo Rappuoli, Colle Val D'Elsa, both of Italy

[73] Assignee: Sclavo S.p.A., Siena, Italy

[21] Appl. No.: 822,092

[22] Filed: Jan. 17, 1992

[51] Int. Cl.$^5$ .................. C12P 21/00; C12N 15/22; C07K 15/26

[52] U.S. Cl. .................. 424/85.6; 530/351; 530/416; 435/69.51

[58] Field of Search .............. 530/351, 416; 424/85.8, 424/85.6; 435/69.51

[56] References Cited

U.S. PATENT DOCUMENTS 4,765,903 8/1988 D'Andrea et al. .................. 530/351
4,808,523 2/1989 Revel et al. .................. 424/85.6
5,004,605 4/1991 Hershenson et al. .............. 530/351
5,037,644 8/1991 Shaked et al. .................. 514/21

FOREIGN PATENT DOCUMENTS 0011435 5/1980 European Pat. Off. .
0287075 10/1988 European Pat. Off. .
0301314 2/1989 European Pat. Off. .
0446850 9/1991 European Pat. Off. .
2061285 5/1981 United Kingdom .

*Primary Examiner*—Howard E. Schain
*Assistant Examiner*—P. Lynn Touzeau
*Attorney, Agent, or Firm*—Stevens, Davis, Miller & Mosher

[57] ABSTRACT

A process is described for the purification of recombinant human beta interferon which comprises the use of three chromatographic stages carried out in series, utilizing as stationary phases: glass particles of controlled porosity, cation exchange polymer resins and polymer resins able to complex heavy metals.

11 Claims, No Drawings

PROCESS FOR THE PURIFICATION OF RECOMBINANT HUMAN BETA INTERFERON, BETA INTERFERON THUS PURIFIED AND PHARMACEUTICAL COMPOSITIONS WHICH CONTAIN IT

FIELD OF THE INVENTION

A process is described for the purification of recombinant rHu-β-IFN consisting of three successive chromatographic stages in which the following stationary phases are used: glass particles of controlled porosity (CPG), cation exchange polymer resins and polymer resins able to complex heavy metals (MCC).

STATE OF THE ART

Human beta interferon (Hu-β-IFN) is a glycoprotein with a molecular weight (MW) of 23,000 daltons, of which the amino-acid sequence was determined by K. Hosoi et al. [J. Interferon Res., 8, pp 375-384 (1988)] and the glucoside sequence was reported by Y. Kagawa et al. [J. Biol. Chem., 263, pp 17508-17515 (1988)]. It is a protein secreted by fibroblasts in response to a viral or bacterial infection, or exposure to foreign cells, macromolecules or RNA. In particular, it inhibits the proliferation of infected cells and stimulates the immune system. The specific antiviral activity of homogeneous Hu-β-IFN is considered to be between $3 \times 10^8$ and $1 \times 10^9$ iu/mg (international units per milligram of total protein) inclusive (see U.S. Pat. No. 4,289,689 and EP-A-94 672).

Because of its activity, Hu-β-IFN is regarded as a promising active principle not only in the treatment and prophylaxis of viral diseases such as hepatitis B, herpes, influenza etc, but also in the treatment of tumoral conditions such as encephaloma and leukaemia.

Hu-β-IFN may be produced from cultures of human fibroblasts maintained under superinduction conditions, for example with poly (I) poly (C) (polyribosinic and polyribocytidylic acid). Its subsequent purification is carried out principally using chromatographic methods. In spite of the various purification techniques used, however, the very low yields obtained from fibroblasts have prevented the availability of large amounts of product.

To overcome this problem, recombinant human beta interferons (rHu-β-IFN) were obtained from cultures of host organisms (selected from groups of bacteria, yeasts or mammal cells) transformed with an expression vector containing the Hu-β-IFN coding gene. The purification of rHu-β-IFN follows the same principle as that of natural interferon, even though conditions are often very different due to the presence of the host cell's own proteins and substances derived from the culture medium, and the different chemical nature of rHu-β-IFN as a result of the different glucoside composition provided by each host cell. The most commonly used purification techniques include: immunoaffinity chromatography using monoclonal antibodies [J. Utsumi et al., J. Biochem., 101, pp 1199-1208 (1987)]; reverse phase chromatography [J. Utsumi et al., J. Biochem., 181, pp 545-553 (1989)]; chromatography with metal chelating agents as the stationary phase (MCC) (U.S. Pat. No. 4,551,271).

Recently, tumoral cells from Chinese hamster ovaries (CHO) have been used for the production of recombinant human beta interferon CHO-rHu-β-IFN [H. S. Conradt et al., J. Biol. Chem., 262, pp 14600-14605 (1987); Y. Chermajobsky et al., DNA 3, pp 297-308 (1984); F. McCormick et al., Mol. Cell. Biol., 4, pp 166-172 (1984)]. These cells have the advantage of allowing the protein expressed in the culture medium to be obtained with a carbohydrate composition largely similar to that of natural proteins from fibroblasts. The purification methods for CHO-rHu-β-IFN are analogous to those used for the cases previously indicated, that is: affinity chromatography with Blue Sepharose, immunoaffinity chromatography with monoclonal antibodies and reverse phase chromatography [(J. Utsumi et al., J. Biochem., 181, pp 545-553 (1989)]; absorption chromatography on CPG and ion exchange chromatography (O. Protasi et al., EPA-0446850 filed on Dec. 3, 1991.

In the case of recombinant interferons, the aforesaid purification techniques do not fully satisfy the requirements of large scale production in that the use of affinity or immunoaffinity chromatography, which enables homogeneous proteins to be obtained, is very expensive and involves considerable process operation and validation problems. These problems are greatly reduced if stationary phases of inorganic or synthetic origin are used although up to the present time these have not enabled a recombinant Hu-β-IFN product of the desired purity to be obtained. It has therefore been sought to combine chromatographic purification stages which, by using inorganic matrices such as CPG and synthetic matrices such as Superose IDA for MCC use, enable CHO-rHu-β-IFN to be obtained with a purity comparable with that obtained by affinity chromatography, but with the aforesaid advantages typical of these phases. However, a serious obstacle to combining CPG and MCC chromatographic techniques in series has up to now been the fact that the product adsorbed onto CPG must be eluted at acid pH and the subsequent adsorption onto MCC requires a neutral pH, whereas variations in pH from acid to neutral values are known to result in complete deactivation of CHO-rHu-β-IFN [Y. K. Tan et al., J. Biol. Chem., 254, pp 8067-8073 (1979)]. The addition of additives such as human serum albumin, polyethylene glycol etc, which reduce the level of deactivation, have the drawback of obstructing the subsequent purification phases and must therefore be removed.

Furthermore it should be noted that Hu-β-IFN in MCC is normally eluted either with solutions which contain strong complexing agents (i.e. able to detach the metal bound to the column) (JP-A-8281505) or with solutions of acid pH (U.S. Pat. No. 4,551,271). Both these methods have various drawbacks. In the first case, the complexing agent contained within the eluent removes not only Hu-β-IFN but also the heavy metal, which contaminates the purified product so that the column must be regenerated after each run. The second method results in a lower recovery in terms of biological activity, and in addition the purified product is collected in an acid environment, making it unsuitable for direct injection. The use of solutions of imidazole (a weak complexing agent) as the eluent for Chelating Sepharose Fast Flow IDA $Me^{2+}$ (Pharmacia) as the stationary phase is also reported in the literature [W. von Muenchausen et al., J. Interferon Res., 8, pp PI-47 (1988)], but again, even with low imidazole concentrations in the eluent, there is a continuous release of metal and hence the aforesaid drawbacks apply.

DETAILED DESCRIPTION OF THE INVENTION

The process according to the present invention enables CHO-rHu-β-IFN to be purified on a large scale while obviating the aforesaid difficulties by using a strong or weak cationic stationary phase which enables the pH of a CHO-rHu-β-IFN solution originating from passage through a CPG column (at acid pH as previously stated) to be increased, thus making it suitable for passage through an MCC column with no loss of interferon activity.

The process according to the present invention comprises a first stage of purification through a chromatography column packed with glass particles of controlled porosity (CPG).

The supernatant derived from a culture of CHO cells transformed using an expression vector containing the Hu-β-IFN gene is firstly filtered to obtain a solution with a specific activity of $1-2 \times 10^5$ iu/mg at a concentration of $1-2 \times 10^5$ iu/ml, and is then fed into a CPG column at a linear flow rate of 1-3 cm/min in a quantity of $30-70 \times 10^6$ iu of CHO-rHu-β-IFN per gram of stationary phase. The column is then subjected to the following washes: water, pH 7; aq. NaCl solution; water, pH 7. The products which remain adsorbed after the washes, including CHO-rHu-β-IFN, are eluted with a solution of acetic acid at a concentration of between 1 and 50 mM at a linear flow rate of 0.25-1 cm/min.

After this stage a solution of CHO-rHu-β-IFN is obtained at a concentration of between $1-10 \times 10^6$ iu/ml with a specific activity of $1-5 \times 10^7$ iu/mg.

The eluate from the CPG column containing acetic acid is fed into a cation exchange column, for example CM-Sepharose Fast Flow (Pharmacia) or CM-Fractogel (Merck) preconditioned with sodium acetate at pH 4.0 or with a dilute acetic acid solution, at a linear flow rate of 1-10 cm/min and at a quantity of $4-6 \times 10^8$ per ml of stationary phase.

The mixture of products which remain adsorbed onto the cation exchange column, including CHO-rHu-β-IFN, is then eluted with a solution of high ionic strength containing NaCl>0.2M, sodium or potassium phosphate buffer at pH 7 and possibly a weak complexing agent such as imidazole (1-12 mM), to obtain a solution of CHO-rHu-β-IFN with a specific activity of $1-5 \times 10^7$ iu/mg and a concentration of $10-40 \times 10^6$ iu/ml.

This solution, either as such if it already contains the weak complexing agent or with the possible addition of said complexing agent, in a quantity so as to obtain a final concentration of between 1 and 12 mM, is fed into a column containing as stationary phase a polymer resin capable of complexing heavy metals (MCC), in which the resin complexing agent is for example iminodiacetic acid (IDA), such as Chelating Superose IDA-$Me^{2+}$, at a linear flow rate of between 1 and 3 cm/min in a quantity of $2.5-4 \times 10^9$ iu/ml of stationary phase.

By feeding this eluent CHO-rHu-β-IFN remains adsorbed, while most of the impurities are eluted away.

On termination of the feed, the MCC column is washed with a 15 mM solution of weak complexing agent, 0.5M of NaCl and 20 mM of sodium or potassium phosphate buffer at pH 7. During this stage a quantity of CHO-rHu-β-IFN (<3%) is eluted together with the final impurities adsorbed on the MCC. If required, this CHO-rHu-β-IFN can be recovered by adding it as such to an unpurified CHO culture before passing it through the CPG column.

Elution of the MCC column is carried out with a >20 mM solution of a weak complexing agent and up to a concentration compatible with the chromatographic conditions, 0.5M solution of NaCl and 20 mM of sodium or potassium phosphate buffer at pH 7.0.

The interferon collected in the eluate is homogeneous on RP-HPLC and SDS-PAGE analysis, with a specific activity of $3-5 \times 10^8$ iu/mg and a concentration of $20-30 \times 10^6$ iu/ml.

If required, any weak complexing agent present in the eluate can be eliminated by the normal salt removal methods described in the literature, such as molecular exclusion chromatography, ultrafiltration etc. As an alternative, a convenient method is to elute the CHO-rHu-β-IFN from the MCC column with eluents containing the weak complexing agent at pH 4, adsorb it onto an ion exchange column identical to those used after CPG chromatography, wash the column with $H_2O$ at pH 7 and finally elute the adsorbed interferon with a solution containing NaCl at a concentration of between 0.1 and 0.5M and sodium or potassium phosphate at a concentration of between 0.01 and 0.1M at pH 7.

To the eluate solution are added human serum albumin at 0.1 to 7.0 mg per million units of interferon and a sugar of the type commonly used as stabilizers, such as mannitol, lactose, dextrose, galactose, saccharose or trehalose at a concentration of between 2 and 25 mg per million units of lyophilized product.

To avoid the presence of traces of metal which may be released by the MCC into the final product, the final solution is made to pass at a linear flow rate of between 0.5 and 3 cm/min through a stationary phase able to scavenge any metals present, such as Chelating Sepharose FFIDA or Chelating Superose IDA.

The product thus obtained is stable and suitable for preparing pharmaceutical products useful for the treatment of viral infections and tumours and as an immunomodulator. The product obtained by the process according to the invention can be administered as such or in combination with suitable pharmacologically acceptable carriers and excipients, either topically (for example as ocular instillations and ointments), intramuscularly, intralesionally or intravenously.

The dosage, to be established according to the requirements of the patient and the method of treatment, can be between 1 and 20 million units per application.

The antiviral activity of CHO-rHu-β-IFN is calculated on the basis of the reduction in cytopathic effect using the virus VSV (vescicular stomatitis virus) and the human cell line HT-10-80 [J. A. Armstrong, Meth. in Enzymol., 78, pp 381-387 (1981)].

EXPERIMENTAL PART

EXAMPLE 1

Purification of CHO-rHu-β-IFN 1000 l of a CHO-rHu-β-IFN solution with a specific activity of $1 \times 10^5$ iu/mg and a concentration of 120,000 iu/ml, obtained from a microcarrier culture of the Chiron CHOB-IFNg 454 cell line derived from the transfection of the line CHO D×B11 with plasmid pSAD 2B IFNg 1, are fed at a flow rate of 50 l/h into a column (252 id×50 mm) packed with the stationary phase CPG-500 (Elettro Nucleonics), column volume (Vc) 2500 ml.

On termination of the feed, the column is washed with 3 Vc of water at pH 7, then with 3 Vc of a 1.4M NaCl solution and finally with 10 Vc of water at pH 7.

The mixture of products which remain adsorbed onto the column, including CHO-rHu-$\beta$-IFN, is eluted with 16 Vc of a 5 mM AcOH pH 3.2 solution, at a flow rate of 12.5 l/h.

This latter eluate, collected in a single container and containing CHO-rHu-$\beta$-IFN at a concentration of $2.4 \times 10^6$ iu/ml and with a specific activity of $1.3 \times 10^7$ iu/mg, is fed as such at a flow rate of 1.25 l/h into a column (100 id $\times$ 25 mm) packed with the CM-Sepharose Fast Flow (Pharmacia) stationary phase (Vc=200 ml) preconditioned with an aqueous 5 mM acetic acid solution. The column is then washed with 10 Vc of water at pH 7.

All the products which remain adsorbed onto the column, including CHO-rHu-$\beta$-IFN, are eluted with 30 Vc of a 10 mM solution of imidazole, 0.5M of NaCl and 20 mM of sodium phosphate buffer at pH 7.

This eluent phase, collected in a single container and containing CHO-rHu-$\beta$-IFN at a concentration of $16 \times 10^6$ iu/ml with a specific activity of $1.5 \times 10^7$ iu/mg, is fed at a flow rate of 0.9 l/h into a column (35 id $\times$ 30 mm) packed with the Chelating Superose IDA $Cu^{2+}$ (Pharmacia) stationary phase (Vc=29 ml).

The column is washed with 2 Vc of a 15 mM solution of imidazole, 0.5M of NaCl and 20 mM of sodium phosphate buffer at pH 7. $2.5 \times 10^7$ iu/ml of CHO-rHu-$\beta$-IFN were found in the eluate from this wash.

The CHO-rHu-$\beta$-IFN which remains adsorbed after this latter wash is eluted from the column with 100 Vc of a 30 mM solution of imidazole, 0.5M of NaCl and 20 mM of sodium phosphate buffer at pH 7.

The resulting solution is pumped at a flow rate of 1.25 l/h into a 35 id $\times$ 10 mm column packed with Chelating Superose IDA to sequester any traces of copper. In this latter stage the eluent is collected in a single container and contains CHO-rHu-$\beta$-IFN of >98% purity as determined by RP-HPLC and SDS-PAGE analysis, having a specific activity of $3.8 \times 10^8$ iu/mg and a concentration of $20 \times 10^6$ iu/ml.

The overall yield of the purification process is 48.8%. Albumin in a quantity of 0.5 mg and trehalose in a quantity of 5 mg per million units are added to the solution after which it is lyophilized and stored at $-20°$ C.

EXAMPLE 2

Purification of CHO-rHu-$\beta$-IFN and removal of imidazole

The procedure is identical to that described in EXAMPLE 1 except that the CHO-rHu-$\beta$-IFN is eluted from the Superose-IDA-$Cu^{2+}$ column with 100 Vc of a 30 mM solution of imidazole, 0.5M of NaCl and 20 mM of phosphate buffer at pH 4. The eluate, collected in a single container, has a specific activity of $3.8 \times 10^8$ and a concentration of $18.5 \times 10^6$ iu/ml, is fed at a flow rate of 1.25 l/h into a column (100 id $\times$ 25 mm) packed with the CM-Sepharose Fast Flow stationary phase (Vc=200 ml). The column is then washed with 10 Vc of $H_2O$ at pH 7 and the interferon still adsorbed is finally eluted with 15 Vc of a 0.15M solution of NaCl solution and 0.1M phosphate buffer at pH 7 at a flow rate of 0.75 l/h. The resulting solution is pumped at a flow rate of 0.75 l/h into a 35 id $\times$ 10 mm column packed with Chelating Superose IDA to remove any traces of copper. In this latter stage, the eluent is collected in a single container and contains CHO-rHu-$\beta$-IFN at >98% purity as determined by RP-HPLC and SDS-PAGE analysis, with a specific activity of $3.8 \times 10^8$ iu/mg and a concentration of $19 \times 10^6$ iu/ml.

The overall yield of the purification process is 46.4%. Albumin in a quantity of 0.5 mg per million units is added to the solution which is then lyophilized and stored at $-20°$ C.

We claim:

1. A process for the purification of CHO-rHu-$\beta$-IFN comprising the following steps:
   a) feeding a solution of CHO-rHu-$\beta$-IFN, obtained from a culture of chinese hamster ovary (CHO) cells transformed using an expression vector containing the Hu-$\beta$-IFN gene, into a chromatographic column packed with glass particles of controlled porosity (CPG), eluting products including CHO-rHu-$\beta$-IFN, which remain adsorbed after washing, with an acetic acid solution at a concentration of between 1 and 50 mM to obtain on eluate containing CHO-rHu-$\beta$-IFN;
   b) feeding the eluate obtained from step a), into a cation exchange column, eluting CHO-rHu-$\beta$-IFN, which remains adsorbed onto the cation exchange column, with a solution of high ionic strength, containing NaCl>0.2M, phosphate buffer at pH 7.0 and a weak complexing agent consisting essentially of imidazole to obtain a solution of CHO-rHu-IFN;
   c) feeding the solution obtained from step b), containing said weak complexing agent, into a column packed with a Chelating Superose IDA stationary phase as a polymer resin capable of complexing heavy metals (MCC), in which the resin complexing agent is iminodiacetic acid (IDA), eluting the MCC column with a solution of said weak complexing agent and a solution of NaCl and a phosphate buffer at pH 7.0 and recovering an eluate containing CHO-rHu-IFN;
   d) optionally removing said weak complexing agent contained in the eluate;
   e) optionally removing trace metals using a metal scavenging resin selected from a group consisting of Chelating Sepharose FFIDA and Chelating Superose IDA; and
   f) adding human serum albumin as a lyophilization protection agent and sugars as stabilizers for the lyophilized product.

2. A process as claimed in claim 1, wherein the removal of the weak complexing agent in accordance with step d) is achieved by eluting the MCC column in step c) at pH 4, adsorbing the eluate on a cation exchange column identical to that used in the step following CPG chromatography, washing said column with water at pH 7.0 and finally eluting adsorbed interferon with a solution of NaCl at a concentration of between 0.1 and 0.5M and phosphate buffer at a concentration of between 0.01 and 0.1M at pH 7.0.

3. A process as claimed in claim 1, wherein the weak complexing agent is imidazole at a concentration of between 1 and 12 mM.

4. A process as claimed in claim 2, wherein the weak complexing agent is imidazole at a concentration of 30 mM.

5. A process as claimed in claim 1, wherein the concentration of the acetic acid eluent solution of step a) is between 5 and 20 mM.

6. A process as claimed in claim 1, wherein the solution of high ionic strength of step b) also contains imidazole in a quantity of 1-12 mM.

7. A process as claimed in claim 1, wherein the cation exchange column of step b) contains a weak cation exchange resin.

8. A process as claimed in claim 1, wherein the cation exchange column of step b) contains a strong cation exchange resin.

9. A process as claimed in claim 1, wherein in step a) the column is subjected to the following washings: water pH 7.0, aqueous NaCl solution, water pH 7.0.

10. A process as claimed in claim 1, wherein the sugar of step f) is selected from a group consisting of mannitol, lactose, dextrose, galactose, saccharose and trehalose.

11. A process as claimed in claim 1, wherein the concentration of human serum albumin of step f) is between 0.1 and 7 mg per million units of interferon and the sugar concentration is between 2 and 25 mg per million units.

* * * * *